United States Patent [19]

Imai

[11] 4,220,764

[45] Sep. 2, 1980

[54] PREPARATION OF TERTIARY HETEROCYCLIC AMINES

[75] Inventor: Tamotsu Imai, Mt. Prospect, Ill.

[73] Assignee: Uop Inc., Des Plaines, Ill.

[21] Appl. No.: 971,284

[22] Filed: Dec. 20, 1978

[51] Int. Cl.$^2$ .......................................... C07D 295/02
[52] U.S. Cl. .................................. 544/178; 544/404; 546/246; 546/184; 548/262; 260/313.1
[58] Field of Search ................ 544/178, 404; 546/184, 546/246; 548/262; 260/308 R, 313.1

[56] References Cited

U.S. PATENT DOCUMENTS

| | | | |
|---|---|---|---|
| 2,422,632 | 6/1947 | Olin et al. | 260/563 R |
| 2,497,310 | 2/1950 | Larson | 260/585 D |
| 3,513,200 | 5/1970 | Biale | 260/576 |
| 3,758,586 | 9/1973 | Coulson | 260/585 D |
| 3,864,382 | 2/1975 | aus der Funten et al. | 260/585 C |

*Primary Examiner*—Henry R. Jiles
*Assistant Examiner*—R. W. Ramsuer
*Attorney, Agent, or Firm*—James R. Hoatson, Jr.; Raymond H. Nelson; William H. Page, II

[57] ABSTRACT

Tertiary amines may be prepared by reacting an olefinic compound, carbon monoxide, hydrogen and a heterocyclic compound containing at least one nitrogen atom which possesses at least one hydrogen atom in the presence of a rhodium- or ruthenium-containing catalyst at temperatures in the range of from about 50° to about 350° C. and a pressure in the range of from about 10 to about 300 atmospheres. The reaction may be exemplified by reacting undecene, carbon monoxide, hydrogen and morpholine in the presence of rhodium chloride to prepare N-dodecylmorpholine.

7 Claims, No Drawings

PREPARATION OF TERTIARY HETEROCYCLIC AMINES

BACKGROUND OF THE INVENTION

Heretofore tertiary amines have been prepared in a wide variety of reactions utilizing various metal-containing compounds as catalysts. For example, U.S. Pat. No. 3,091,641 discloses a process for preparing tertiary amines in which a secondary amine and an aliphatic ketone are reacted with carbon monoxide and water in the presence of an iron carbonyl catalyst such as iron pentacarbonyl or biscyclopentadienyl diiron tetracarbonyl. Another U.S. Patent, namely, U.S. Pat. No. 2,497,310 discloses the synthesis of amines in which an unsaturated compound, carbon monoxide, hydrogen and ammonia or a substitute ammonia are reacted in the presence of a cobalt catalyst although other catalysts which possess hydrogenation properties such as nickel, ruthenium, iron and copper may also be used. Another prior art reference, namely, U.S. Pat. No. 3,947,458 is drawn to a process for preparing amines in which nitrogen-containing compounds and an olefin along with carbon monoxide and water are reacted in the presence of a catalyst comprising iron pentacarbonyl and a rhodium compound. In like manner, U.S. Pat. No. 3,234,283 also discloses a process for the preparation of trialkyl amines in which an olefin is reacted with carbon monoxide, hydrogen and a dialkyl amine in the presence of a catalyst consisting essentially of cobalt carbonyl trihydrocarbonphosphene. The hydrocarbon content of the catalyst is limited to trihydrocarbons containing a total of up to about 30 carbon atoms, the number of carbon atoms in any one of said hydrocarbon radicals not exceeding 18. Other prior art patents include U.S. Pat. No. 3,758,586 in which ethylene is reacted with secondary aliphatic amines in the presence of rhodium or iridium catalysts to form a tertiary amine in which one of the substituents is, of necessity, ethylene; U.S. Pat. No. 3,513,200 in which the preparation of tertiary amines is accomplished by reacting a secondary amine containing from 2 to about 20 carbon atoms with an aliphatic hydrocarbon olefin containing from about 2 to about 20 carbon atoms, as well as carbon monoxide and hydrogen in the presence of a complex catalyst comprising a Group VIII noble metal hydride in complex with a biphyllic ligand, said ligand containing phosphoric, arsenic or antimony; U.S. Pat. No. 3,412,158 which is drawn to a process for the preparation of aliphatic amines from the reaction of lower molecular weight olefins and ammonia, the primary product comprising a primary amine rather than a tertiary amine; U.S. Pat. No. 2,501,509 which is drawn to the preparation of amines by heating an ammonia type compound with a hydrocarbon olefinic compound utilizing an alkali metal catalyst such as sodium, this reference requires the presence of an organic liquid diluent for the olefinic reactant; and U.S. Pat. No. 2,422,631 in which aliphatic amines are produced by reacting an olefin, an oxide of carbon, hydrogen and an aminating agent in the presence of a hydrogenation-dehydration catalyst, examples of these catalysts being zinc chromate, zinc tungstate, chromium phosphate, cobalt oxide, iron oxide, etc.

In contradistinction to the above reactions, it will be hereinafter shown in greater detail that tertiary amines may be synthesized by utilizing a particular rhodium- or ruthenium-containing catalyst to obtain an economically attractive conversion of the olefin compound with an economically attractive selectivity to the desired product.

SPECIFICATION

This invention relates to a process for the synthesis of tertiary amines. More specifically, the invention is concerned with a process for synthesizing tertiary amines by reacting an olefinic compound with a nitrogen-containing compound, and specifically a heterocyclic compound which contains at least one nitrogen atom in the ring, said nitrogen atom in the ring possessing at least one hydrogen atom, along with carbon monoxide and hydrogen in the presence of certain catalytic compositions of matter.

Tertiary amines will find a wide variety of uses in the chemical field. For example, these compounds may be used in agricultural applications, acting as an inert surfactant for herbicides; for use in corrosion inhibition and crude oil pipelines; in cosmetic formulation; leather processing; paint formulation; secondary oil recovery; mineral separation (cationic flocculation or flotation), etc. A specific compound, namely, tributylamine is used as a solvent, as an intermediate in the preparation of other chemicals and as an inhibitor in hydraulic fluids. In view of these important chemical uses, it is therefore necessary to effect the preparation of the tertiary amines in an economically feasible manner, said process requiring a relatively quantitative conversion of the olefins which are used in the process as well as requiring a high percentage of selectivity to the desired compound. These objectives may be attained by utilizing the process of the present invention in which the reaction is effected in the presence of certain catalytic compositions of matter of the type hereinafter set forth in greater detail.

It is therefore an object of this invention to provide a process for the synthesis of tertiary amines.

A further object of this invention is to provide a process for the synthesis of tertiary amines whereby economical, attractive yields of the desired product are obtained.

In one aspect an embodiment of this invention resides in a process for the preparation of a tertiary amine which comprises reacting an olefinic compound, carbon monoxide, hydrogen and a heterocyclic compound containing at least one nitrogen atom which possesses at least one hydrogen atom in the presence of a rhodium- or ruthenium-containing catalyst at reaction conditions, and recovering the resultant tertiary amine.

A specific embodiment of this invention is found in a process for the preparation of a tertiary amine which comprises reacting undecene, carbon monoxide, hydrogen and morpholine at a temperature in the range of from about 50° to about 350° C. and a pressure in the range of from about 10 to about 300 atmospheres in the presence of a catalyst comprising rhodium chloride, and recovering the resultant N-dodecylmorpholine.

Other objects and embodiments will be found in the following further detailed description of the present invention.

As hereinbefore set forth the present invention is concerned with a process for the synthesis of tertiary amines. These compounds are prepared by reacting an olefinic compound, carbon monoxide, hydrogen and a heterocyclic compound containing at least one nitrogen atom which possesses one or two hydrogen atoms. The nitrogen atom in addition to being a constituent of the heterocyclic ring may also be present on a side chain which is attached to the heterocyclic ring. The heterocyclic compound in addition to containing at least one nitrogen atom may also contain oxygen and/or sulfur atoms in the ring along with the carbon atoms, there being at least two carbon atoms present in the ring. The reaction will be effected in the presence of certain catalytic compositions of matter hereinafter set forth in greater detail and in the absence of added water. The reaction conditions which are employed to produce the desired results will include temperatures in the range of from about 50° to about 350° C. and pressures in the range of from about 10 to about 300 atmospheres. In the preferred embodiment of the invention, the pressures which are employed will be the autogeneous pressures resulting from the presence of carbon monoxide and hydrogen as well as the olefinic compounds, if in gaseous form, in the reaction mixture, although it is also contemplated within the scope of this invention that the pressures resulting from the use of carbon monoxide and hydrogen will comprise only a partial operating pressure, the remainder being provided for by the introduction of a substantially inert gas such as nitrogen, helium, argon, etc., into the reaction vessel. Other reaction conditions which are present during the synthesis of the tertiary amines will include mole ratios of the various components. For example, the carbon monoxide which is employed in the reaction mixture will be present in a mole ratio in the range of from about 1:1 to about 100:1 moles of carbon monoxide/mole of olefinic compound, 1:1 to about 5:1 moles of olefinic compound/mole of heterocyclic compound; and from about 0.5:1 to about 3:1 moles of hydrogen/mole of carbon monoxide. The mole ratio of olefinic compound to mole of heterocyclic compound will be dependent upon the number of hydrogen atoms attached to nitrogen atoms which are available for alkylation.

Examples of olefinic compounds which may be employed as one of the components of the reaction mixture will include open chain compounds containing from 2 to about 30 carbon atoms such as ethylene, propylene, 1-butene, 2-butene, 1-pentene, 2-pentene, 1-hexene, 2-hexene, 3-hexene, 1-heptene, 2-heptene, 3-heptene, 1-octene, 2-octene, 3-octene, 4-octene, the isomeric straight chain nonenes, decenes, undecenes, dodecenes, tridecenes, tetradecenes, pentadecenes, hexadecenes, heptadecenes, octadecenes, nonadecenes, eicosenes, henicosenes, docosenes, tricosenes, tetracosenes, pentacosenes, hexacosenes, heptacosenes, octacosenes, nonacosenes, triacontenes, etc., as well as branched chain isomers thereof; cycloalkenes such as cyclopentene, cyclohexene, cycloheptene, cyclooctene, etc.; diolefines such as 1,3-butadiene, 1,3-pentadiene, 1,3-hexadiene, 2,4-hexadiene, 1,3-heptadiene, 2,4-heptadiene, the isomeric octadienes, nonadienes, decadienes, undecadienes, dodecadienes, etc.

The aforesaid olefinic compounds are reacted with a heterocyclic compound containing at least one nitrogen atom possessing at least one hydrogen atom. The nitrogen atom referred to may be a constituent or part of the heterocyclic ring, or may be a component of a side chain which is attached to the heterocyclic ring. The heterocyclic ring will be made up of carbon and nitrogen, oxygen and/or sulfur atoms, at least two atoms in the heterocyclic ring being carbon. Some specific examples of the heterocyclic compounds which may be employed will include pyrrole, pyrazole, imidazole, 1,2,3-triazole, 1,2,4-triazole, 2,1,3-triazole, 4,1,2-triazole, 1,2,3,4-tetrazole, 1,2,3-dioxazole, 1,3,2-dioxazole, 1,3,2-dioxazole, 1,2,4-dioxazole, 1,3,4-dioxazole, 1,3,4,2-dioxadiazole, 1,2,3-dithiazole, 1,2,4-dithiazole, 1,3,2-dithiazole, 1,3,4-dithiazole, 1,3,2,4-dithiadiazole, piperidine, piperazine, o-isoxazine, o-isothiazine, p-isoxazine, p-isothiazine, morpholine, isoindole, isoindazole, benzimidazole, indazole, 1,2,3-benzotriazole, 2,1,3-benzotriazole, 1,3,4,6-benzotetrazole, 4-aminomethylpiperidine, 4-aminoethylpiperidine, 4-aminopropylpiperidine, 4-aminomethylpyran, 4-aminoethylpyran, 4-aminomethylthiapyran, 4-aminoethylthiapyran, etc. It is to be understood that the aforementioned heterocyclic compounds and olefinic compounds are only representative of the class of compounds which may be employed as reactants, and that the present invention is not necessarily limited thereto.

The reaction between the aforementioned olefinic compounds, heterocyclic compounds containing at least one nitrogen atom which possesses at least one hydrogen atom, carbon monoxide and hydrogen is effected in the presence of certain catalytic compositions of matter, said compositions comprising rhodium- or ruthenium-containing compounds. In the preferred embodiment of the invention, the ruthenium- or rhodium-containing compounds will comprise the metals or the nitrates, halides, halocarbonyls or carbonyl complexes. Specific examples of these compounds which are employed will include rhodium, rhodium nitrate, rhodium chloride, rhodium bromide, rhodium iodide, rhodium fluoride, chlorodicarbonylrhodium dimer, rhodium carbonyl, chlorobis(ethylene)rhodium dimer, ruthenium, ruthenium nitrate, ruthenium chloride, ruthenium bromide, ruthenium iodide, ruthenium fluoride, dichlorotricarbonylruthenium dimer, ruthenium carbonyl, etc.

The process of the present invention may be effected in any suitable manner and may comprise either a batch or continuous type of operation. When a batch type operation is used, a quantity of the olefin and the heterocyclic compounds containing at least one nitrogen atom which possesses at least one hydrogen atom, if in solid or liquid form, is placed in an appropriate pressure resistant apparatus such as an autoclave of the rotating or mixing type which contains a predetermined amount of the rhodium- or ruthenium-containing compound. The autoclave is then sealed and carbon monoxide and hydrogen are charged thereto until the desired operating pressure is reached. Alternatively, as hereinbefore discussed, if higher pressures are to be employed, a portion of the pressure may be afforded by the introduction of a substantially inert gas into the reaction mixture along with the carbon monoxide and hydrogen. After the proper operating pressure has been attained, the autoclave is then heated to the desired operating temperature which may range from about 50° to about 350° C. or more and the apparatus maintained thereat for a predetermined residence time which may range from about 0.5 up to about 10 hours or more in duration. Upon completion of the residence time, heating is discontinued and the autoclave and contents thereof are allowed to return to room temperature. Upon reaching room temperature the excess pressure is discharged, the autoclave is opened and the reaction mixture is recovered therefrom. After separation from the catalyst, the reaction mixture may then be subjected to conventional means of separation whereby the desired tertiary amine is separated from unreacted starting materials and/or unwanted side reaction products which may have been formed and recovered.

It is also contemplated within the scope of this invention that the synthesis of tertiary amines may be accomplished by utilizing a continuous method of operation. When utilizing this type of operation, the olefinic compound and the heterocyclic compounds containing at least one nitrogen atom which possesses at least one hydrogen atom are continuously charged to a reaction zone which is maintained at the proper operating conditions of temperature and pressure, said reaction zone containing a catalyst of the type hereinbefore set forth. In addition, carbon monoxide and hydrogen are also continuously charged to the reaction zone through separate lines or, if so desired, they may be admixed prior to entry into said zone and the resulting mixture charged thereto in a single stream. Upon completion of the desired residence time in the reaction zone, the reactor effluent is continuously withdrawn and subjected to conventional means of separation such as fractional distillation whereby the desired tertiary amine is separated from unreacted starting materials and recovered, while the aforesaid unreacted starting materials may be recycled to the reaction zone to form a portion of the feed stock.

Some specific examples of the types of tertiary amines which may be prepared according to the process of this invention will include N-propylmorpholine, N-butylmorpholine, N-amylmorpholine, N-hexylmorpholine, N-heptylmorpholine, N-octylmorpholine, N-nonylmorpholine, N-decylmorpholine, N-undecylmorpholine, N-dodecylmorpholine, N-tridecylmorpholine, N-tetradecylmorpholine, N-pentadecylmorpholine, N-hexadecylmorpholine, N-heptadecylmorpholine, N-octadecylmorpholine, N-nonadecylmorpholine, N-eicosylmorpholine, N-docosylmorpholine, N-tricosylmorpholine, N-propylpyrrole, N-butylpyrrole, N-amylpyrrole, N-hexylpyrrole, N-heptylpyrrole, N-octylpyrrole, N-nonylpyrrole, N-decylpyrrole, N-undecylpyrrole, N-dodecylpyrrole, N-tridecylpyrrole, N-tetradecylpyrrole, N-pentadecylpyrrole, N-hexadecylpyrrole, N-heptadecylpyrrole, N-octadecylpyrrole, N-nonadecylpyrrole, N-eicosylpyrrole, N-docosylpyrrole, N-tricosylpyrrole, N-propylpiperidine, N-butylpiperidine, N-amylpiperidine, N-hexylpiperidine, N-heptylpiperidine, N-octylpiperidine, N-nonylpiperidine, N-decylpiperidine, N-undecylpiperidine, N-dodecylpiperidine, N-tridecylpiperidine, N-tetradecylpiperidine, N-pentadecylpiperidine, N-hexadecylpiperidine, N-heptadecylpiperidine, N-octadecylpiperidine, N-nonadecylpiperidine, N-eicosylpiperidine, N-docosylpiperidine, N-tricosylpiperidine, N-propyl-1,2,4-triazole, N-butyl-1,2,4-triazole, N-amyl-1,2,4-triazole, N-hexyl-1,2,4-triazole, N-heptyl-1,2,4-triazole, N-octyl-1,2,4-triazole, N-nonyl-1,2,4-triazole, N-decyl-1,2,4-triazole, N-undecyl-1,2,4-triazole, N-dodecyl-1,2,4-triazole, N-tridecyl-1,2,4-triazole, N-tetradecyl-1,2,4-triazole, N-pentadecyl-1,2,4-triazole, N-hexadecyl-1,2,4-triazole, N-heptadecyl-1,2,4-triazole, N-octadecyl-1,2,4-triazole, N-nonadecyl-1,2,4-triazole, N-eicosyl-1,2,4-triazole, N-docosyl-1,2,4-triazole, N-tricosyl-1,2,4-triazole, 1-propyl-4-dipropylaminomethylpiperidine, 1-butyl-4-dipropylaminomethylpiperidine, 1-amyl-4-dipropylaminomethylpiperidine, 1-hexyl-4-dipropylaminomethylpiperidine, 1-heptyl-4-dipropylaminomethylpiperidine, 1-octyl-4-dipropylaminomethylpiperidine, 1-nonyl-4-dipropylaminomethylpiperidine, 1-decyl-4-dipropylaminomethylpiperidine, 1-undecyl-4-dipropylaminomethylpiperidine, 1-dodecyl-4-dipropylaminomethylpiperidine, 1-tridecyl-4-dipropylaminomethylpiperidine, 1-tetradecyl-4-dipropylaminomethylpiperidine, 1-pentadecyl-4-dipropylaminomethylpiperidine, 1-hexadecyl-4-dipropylaminomethylpiperidine, 1-heptadecyl-4-dipropylaminomethylpiperidine, 1-octadecyl-4-dipropylaminomethylpiperidine, 1-eicosyl-4-dipropylaminomethylpiperidine, 1-docosyl-4-dipropylaminomethylpiperidine, 1-tricosyl-4-dipropylaminomethylpiperidine, etc. It is understood that the aforementioned compounds are only representative of the types of tertiary amines which may be prepared according to the process described herein and that the present invention is not necessarily limited thereto.

The following examples are given to illustrate the process of the present invention. However, it is to be understood that these examples are given merely for purposes of illustration and that the present invention is not necessarily limited thereto.

EXAMPLE I

In this example 0.035 gram of a catalyst comprising rhodium chloride was placed in a rocking autoclave. In addition, 28.63 grams of morpholine and 50.24 grams of undecene were also placed in the autoclave. The autoclave was sealed and a 1:1 mixture of carbon monoxide and hydrogen blend gas was charged to the autoclave until an initial pressure of 150 atmospheres was reached. The autoclave was then heated to a temperature of about 150° C. and maintained thereat for a period of 3 hours, during this period the pressure in the autoclave dropping from 187 atmospheres to 149 atmospheres. At the end of the 3 hour period heating was discontinued and the autoclave was allowed to return to room temperature. Upon reaching room temperature the excess pressure was discharged and the reaction mixture was recovered therefrom. The product was subjected to gas liquid chromatographic analysis and elementary analysis which showed that there had been a 100% conversion of the undecene with a 98% selectivity to N-dodecylmorpholine.

EXAMPLE II

In a manner similar to that set forth above, 0.03 gram of a catalyst comprising rhodium chloride along with 12.2 grams of 4(aminomethyl)piperidine and 50.0 grams of undecene were charged to an 850 cc rocking autoclave. The autoclave was sealed and a blend gas comprising 150 atmospheres of a 1:1 mole ratio of carbon monoxide and hydrogen was charged thereto. The autoclave was then heated to a temperature of about 150° C. and maintained thereat for a period of 3 hours, the initial operating pressure of 200 atmospheres dropping to 172 atmospheres during the 3 hour period. Upon completion of the desired residence time, heating was discontinued and the autoclave was allowed to return to room temperature. The excess pressure was discharged, the autoclave was opened, and the reaction mixture was recovered therefrom. The reaction mixture was subjected to gas liquid chromatographic and elementary analysis which determined that there had been a 96.2% conversion of the olefin and a 100% conversion of the amine, the major portion comprising 1-dodecyl-4-didodecylaminomethylpiperidine.

EXAMPLE III

In this example a mixture comprising equimolar proportions of pyrrole and heptene along with a catalyst comprising chlorodicarbonylrhodium dimer may be placed in the glass liner of a rotating autoclave. The autoclave may be sealed and a blend gas consisting of equimolar amounts of carbon monoxide and hydrogen may be charged to the autoclave until the initial operating pressure of 150 atmospheres is reached. Following this the autoclave may then be heated to a temperature of 150° C. and maintained thereat for a period of 3 hours, at the end of which time heating may be discontinued and the autoclave allowed to return to room temperature. Following return to room temperature the autoclave may be opened and the reaction mixture recovered therefrom. Gas liquid chromatographic and elementary analysis may be used to determine the presence of the desired compound comprising N-octypyrrole.

EXAMPLE IV

To the glass liner of a rocking autoclave may be charged piperazine and heptene, said heptene being present in a 2:1 mole ratio of heptene to piperazine. In addition, catalysts comprising chlorobis(ethylene)rhodium dimer may also be added to the autoclave which is thereafter sealed. The autoclave may then be pressured to an initial operating pressure of 150 atmospheres with a 1:1 ratio of carbon monoxide and hydrogen as the blend gas. After reaching the desired operating pressure, the autoclave may then be heated to a temperature of 150° C. and maintained thereat for a period of 3 hours. At the end of the 3 hour period heating may be discontinued and after the autoclave has returned to room temperature the excess pressure may be discharged and the autoclave opened. After recovering the reaction mixture it may be subjected to gas liquid chromatographic and elementary analysis to determine the presence of a major portion of N,N'-dioctylpiperazine.

EXAMPLE V

In this example an equimolar amount of 1,2,4-triazole and docosene may be placed in a rocking autoclave along with a catalyst comprising ruthenium carbonyl. The autoclave is sealed and treated in a manner similar to that set forth in the above examples, that is, by pressuring in 150 atmospheres of a blend gas comprising a 1:1 mole ratio of carbon monoxide and hydrogen. After heating the autoclave to a temperature of 150° C. and maintaining the autoclave thereat for a period of 3 hours, heating may be discontinued and the autoclave allowed to return to room temperature. After return to room temperature, the excess pressure may be discharged, the autoclave opened and the reaction mixture recovered therefrom. Gas liquid chromatographic and elementary analysis may be used to determine the presence of the desired compound, namely, tricosyl-1,2,4-triazole.

I claim as my invention:

1. A process for the preparation of a tertiary amine which comprises reacting an olefinic compound, carbon monoxide, hydrogen and a heterocyclic compound containing at least one nitrogen atom which possesses at least one hydrogen atom in the presence of a rhodium chloride catalyst at reaction conditions, and recovering the resultant tertiary amine.

2. The process as set forth in claim 1 in which said reaction conditions include a temperature in the range of from about 50° to about 350° C. and a pressure in the range of from about 10 to about 300 atmospheres.

3. The process as set forth in claim 1 in which said olefinic compound is undecene, said heterocyclic compound is morpholine, and said tertiary amine is N-dodecylmorpholine.

4. The process as set forth in claim 1 in which said olefinic compound is undecene, said heterocyclic compound is 4-(aminomethyl)piperidine, and said tertiary amine is 1-dodecyl-4-diododecylaminomethylpiperidine.

5. The process as set forth in claim 1 in which said olefinic compound is heptene, said heterocyclic compound is pyrrole, and said tertiary amine is N-octylpyrrole.

6. The process as set forth in claim 1 in which said olefinic compound is heptene, said heterocyclic compound is piperazine, and said tertiary amine is N,N'-dioctylpiperazine.

7. The process as set forth in claim 1 in which said olefinic compound is docosene, said heterocyclic compound is 1,2,4-triazole, and said tertiary amine is tricosyl-1,2,4-triazole.

* * * * *